US010271747B2

United States Patent
Ozawa et al.

(10) Patent No.: US 10,271,747 B2
(45) Date of Patent: Apr. 30, 2019

(54) LIVING-BODY INFORMATION MEASURING DEVICE

(71) Applicant: FUJI XEROX CO., LTD., Tokyo (JP)

(72) Inventors: Hideaki Ozawa, Kanagawa (JP);
Hideyuki Umekawa, Kanagawa (JP);
Tomoaki Kojima, Kanagawa (JP);
Kazuhiro Sakai, Kanagawa (JP);
Manabu Akamatsu, Kanagawa (JP)

(73) Assignee: FUJI XEROX CO., LTD., Minato-ku, Tokyo (JP)

( * ) Notice: Subject to any disclaimer, the term of this patent is extended or adjusted under 35 U.S.C. 154(b) by 362 days.

(21) Appl. No.: 15/229,206

(22) Filed: Aug. 5, 2016

(65) Prior Publication Data

US 2017/0273576 A1    Sep. 28, 2017

(30) Foreign Application Priority Data

Mar. 28, 2016  (JP) ................................ 2016-0644461

(51) Int. Cl.
| | |
|---|---|
| *A61B 5/00* | (2006.01) |
| *A61B 5/021* | (2006.01) |
| *A61B 5/024* | (2006.01) |
| *A61B 5/026* | (2006.01) |
| *A61B 5/0205* | (2006.01) |
| *A61B 5/1455* | (2006.01) |

(52) U.S. Cl.
CPC .......... *A61B 5/0261* (2013.01); *A61B 5/0205* (2013.01); *A61B 5/1455* (2013.01); *A61B 5/7225* (2013.01); *A61B 5/7257* (2013.01); *A61B 5/7278* (2013.01); *A61B 5/021* (2013.01); *A61B 5/02416* (2013.01); *A61B 2562/0233* (2013.01)

(58) Field of Classification Search
CPC ... A61B 5/0261; A61B 5/7225; A61B 5/0205; A61B 5/1455; A61B 5/7278; A61B 5/7257; A61B 5/021; A61B 5/02416; A61B 2562/0233; A61B 5/1451; H01S 5/18344; H01S 5/18347; H01S 5/1835
See application file for complete search history.

(56) References Cited

U.S. PATENT DOCUMENTS 5,490,506 A *  2/1996  Takatani ............... A61B 5/0059
                                                        356/41
6,253,097 B1 * 6/2001  Aronow ............. A61B 5/14552
                                                        600/310
(Continued)

FOREIGN PATENT DOCUMENTS

JP        2008-212258 A      9/2008

*Primary Examiner* — Jacqueline Cheng
*Assistant Examiner* — Abid A Mustansir
(74) *Attorney, Agent, or Firm* — Sughrue Mion, PLLC (57) ABSTRACT

A living-body information measuring device includes plural light-emitting elements, a light-receiving element that is disposed at a position at different distances from the light-emitting elements and that receives reflected light beams that are reflected from a living body when the light-emitting elements emit light beams toward the living body, a control unit that controls the light-emitting elements so that the light-emitting elements successively emit the light beams, and a measurement unit that measures living-body information at plural depths in the living body by using the reflected light beams that are successively received by the light-receiving element.

6 Claims, 9 Drawing Sheets

(56) References Cited

U.S. PATENT DOCUMENTS

| | | | |
|---|---|---|---|
| 2006/0211924 A1* | 9/2006 | Dalke | A61B 5/14552 600/310 |
| 2007/0293767 A1* | 12/2007 | Hwang | A61B 5/0059 600/476 |
| 2011/0027925 A1* | 2/2011 | Ikuta | H01S 5/18311 438/31 |
| 2011/0112387 A1* | 5/2011 | Li | A61B 5/14551 600/324 |
| 2013/0202248 A1* | 8/2013 | Uetake | G02B 6/12 385/14 |

\* cited by examiner

LIVING-BODY INFORMATION MEASURING DEVICE

CROSS-REFERENCE TO RELATED APPLICATIONS

This application is based on and claims priority under 35 USC 119 from Japanese Patent Application No. 2016-064461 filed Mar. 28, 2016.

BACKGROUND (i) Technical Field

The present invention relates to a living-body information measuring device.

(ii) Related Art

Some blood flow sensors, which are examples of living body sensors, measure the blood flow, the amount of a blood component, or the like of a subcutaneous blood vessel, such as a capillary vessel, by emitting a laser beam toward a living body and by receiving a reflected light beam reflected from the living body. It is known that the depth, beneath a skin, of a region that a blood flow sensor measures depends on the distance between a light-emitting element and a light-receiving element. To be specific, it is known that the depth, beneath a skin, of a region that a blood flow sensor measures increases as the distance between the light-emitting element and the light-receiving element increases. In order to increase the amount of information necessary for diagnosis and health care, it is preferable to obtain living-body information at more than one depth.

SUMMARY

According to an aspect of the invention, a living-body information measuring device includes plural light-emitting elements; a light-receiving element that is disposed at a position at different distances from the light-emitting elements and that receives reflected light beams that are reflected from a living body when the light-emitting elements emit light beams toward the living body; a control unit that controls the light-emitting elements so that the light-emitting elements successively emit the light beams; and a measurement unit that measures living-body information at plural depths in the living body by using the reflected light beams that are successively received by the light-receiving element.

BRIEF DESCRIPTION OF THE DRAWINGS

Exemplary embodiments of the present invention will be described in detail based on the following figures, wherein.

DETAILED DESCRIPTION

Hereinafter, exemplary embodiments of the present invention will be described with reference to the drawings. In all of the drawings, elements that perform the same operations or have the same functions will be denoted by the same numerals, and redundant descriptions of such elements will be omitted.

First Exemplary Embodiment

Figure 1:
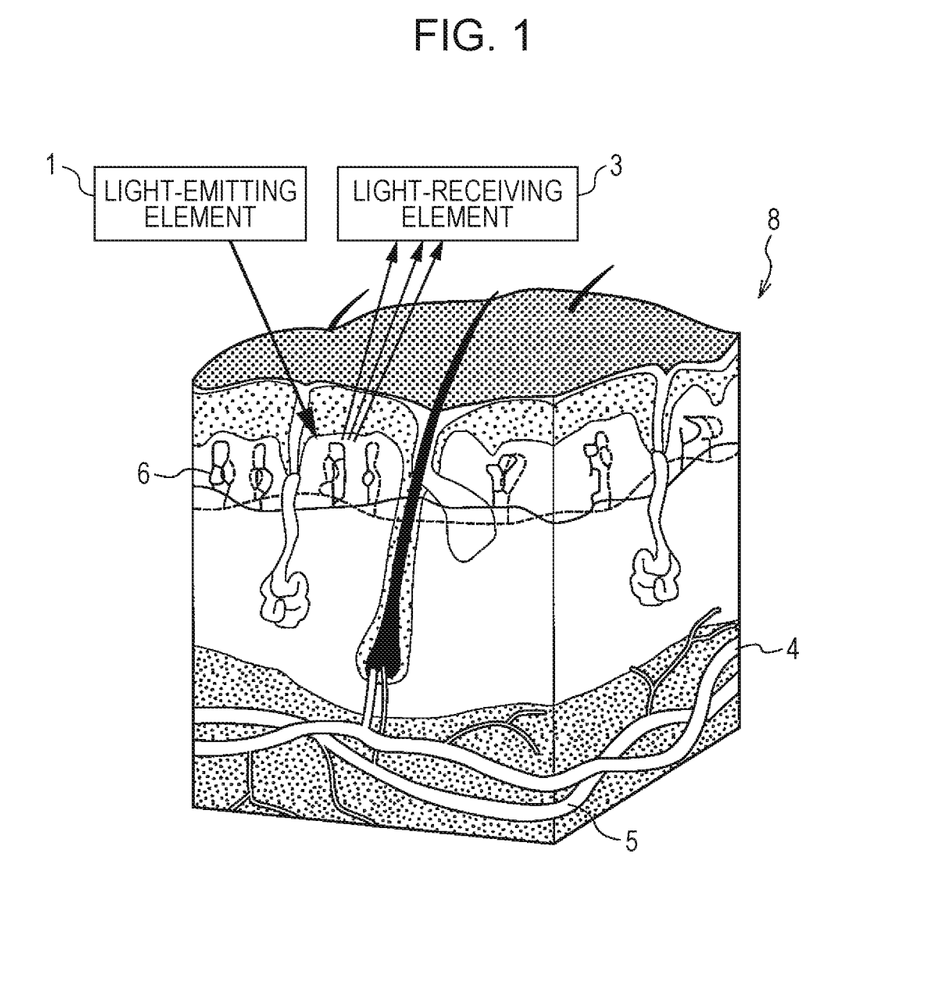
FIG. 1 is a schematic view illustrating an example of measurement of a blood flow.

Referring to FIG. 1, a method of measuring blood flow information, which is an example of living-body information related to blood, will be described.

As illustrated in FIG. 1, blood flow information is measured by emitting light from a light-emitting element 1 toward a patient's body (living body 8); receiving light that is reflected or transmitted by an artery 4, a vein 5, a capillary vessel 6, or the like in the patient's body by using a light-receiving element 3; and by measuring the intensity of the received light, that is, the amount of reflected light or transmitted light received by the light-receiving element 3.

Measurement of Blood Flow Information

Figure 2:
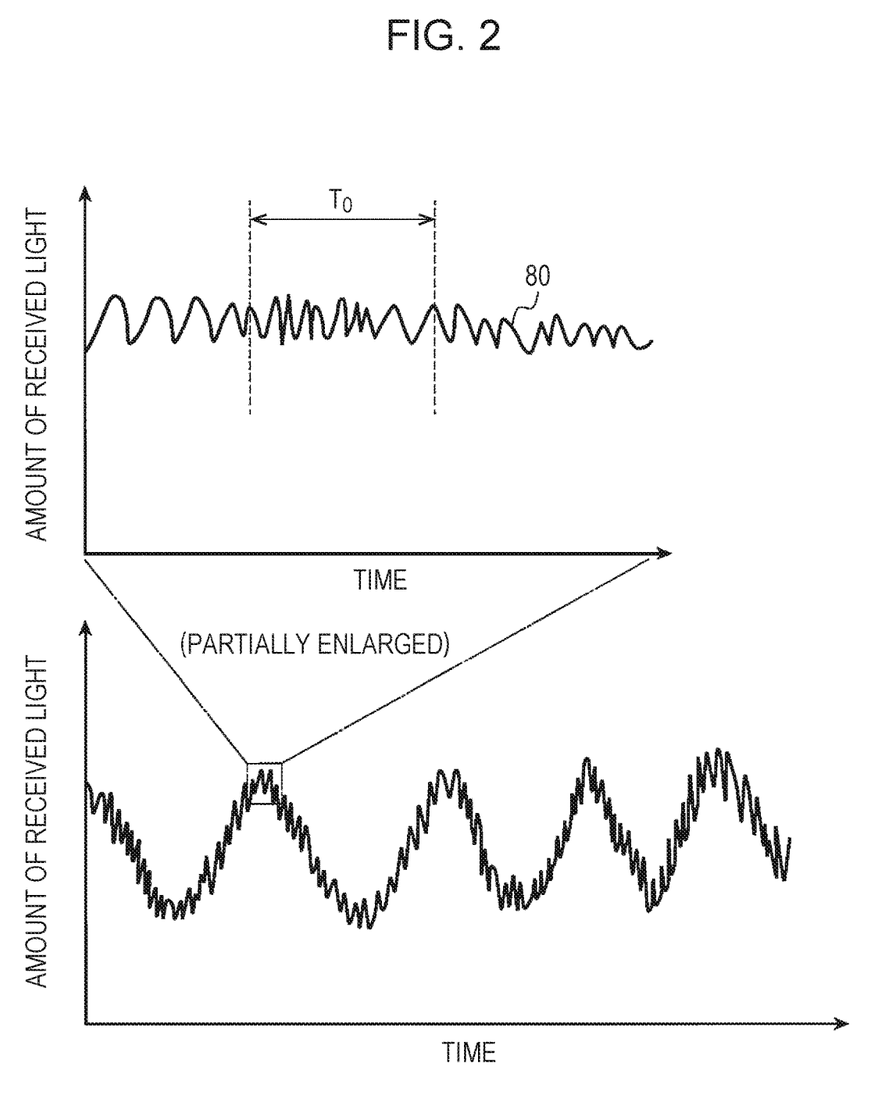
FIG. 2 is a graph illustrating one example of a change in an amount of received light due to reflected light from a living body.

FIG. 2 illustrates graphs showing a curve 80 that represents an example the amount of reflected light received by the light-receiving element 3. In the graph of FIG. 2, the horizontal axis represents the time and the vertical axis represents the output of the light-receiving element 3, that is, the amount of light received by the light-receiving element 3.

As illustrated in FIG. 2, the amount of light received by the light-receiving element 3 changes with time. It is considered that this change occurs due to the following first to third optical phenomena that occur when the living body 8, including blood vessels, is irradiated with light.

The first optical phenomenon is a change in absorption of light that occurs due to a change in the volume of blood existing in a blood vessel that is being measured by pulsation. The blood includes blood cells, such as red blood cells, and the blood moves in a blood vessel, such as the capillary vessel 6. Therefore, when the blood volume changes, the number of blood cells that move in the blood vessel also changes. This change may influence the amount of light received by the light-receiving element 3.

The second optical phenomenon is an influence of a Doppler shift.

Figure 3:
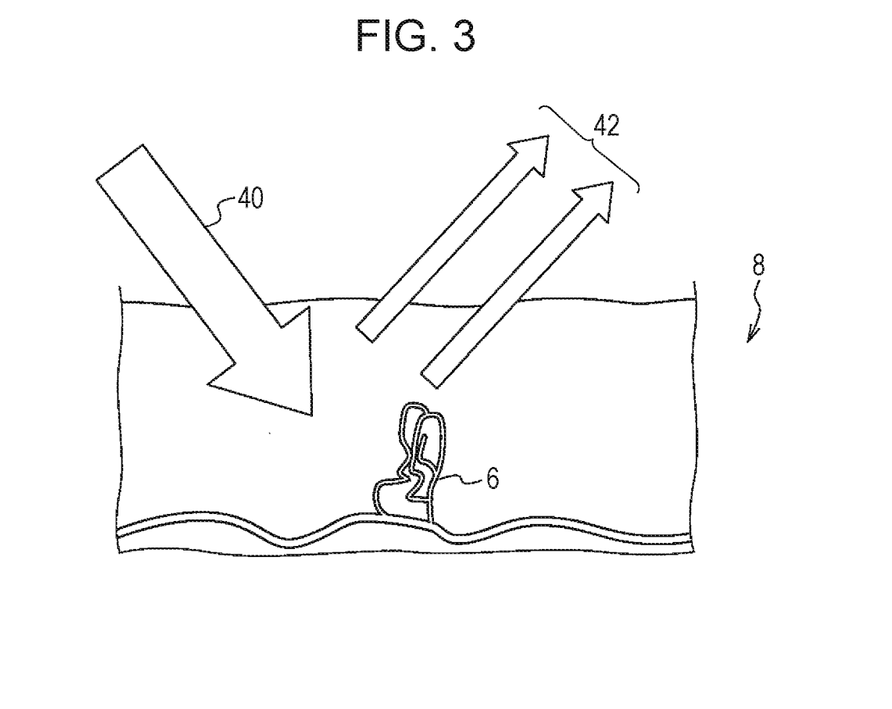
FIG. 3 is a schematic diagram used to explain a Doppler shift that occurs when a blood vessel is irradiated with a laser beam.

FIG. 3 illustrates a case where, for example, the light-emitting element 1 emits a coherent light beam 40, such as a laser beam, having a frequency $\omega_0$ toward a region including the capillary vessel 6, which is an example of a blood vessel. In this case, a Doppler shift, having a frequency difference $\Delta\omega_0$, occurs in a part of a scattered light beam 42 that is generated due to scattering of the coherent light beam 40 by blood cells moving in the capillary vessel 6. The frequency difference $\Delta\omega_0$ is determined by the moving speed of the blood cells. In contrast, another part of the scattered light beam 42 that is generated due to scattering of the coherent light beam 40 by an organ (stationary tissues) that does not include moving components, such as blood cells, has a frequency that is the same as the frequency $\omega_0$ of the emitted light beam. Accordingly, the part of the scattered light 42 having a frequency $(\omega_0+\Delta\omega_0)$, which is scattered by a blood vessel, such as the capillary vessel 6, and the other part of the scattered light 42 having the frequency $\omega_0$, which is scattered by a stationary tissues, interfere with each other. As a result, a beat signal having the frequency difference $\Delta\omega_0$ is observed by the light-receiving element 3, and the amount of light received by the light-receiving element 3 changes with time. The frequency difference $\Delta\omega_0$ of the beat signal observed by the light-receiving element 3, which depends on the moving speed of blood cells, is within a range having an upper limit of several tens of kilohertz.

The third optical phenomenon is an influence of speckles.

Figure 4:
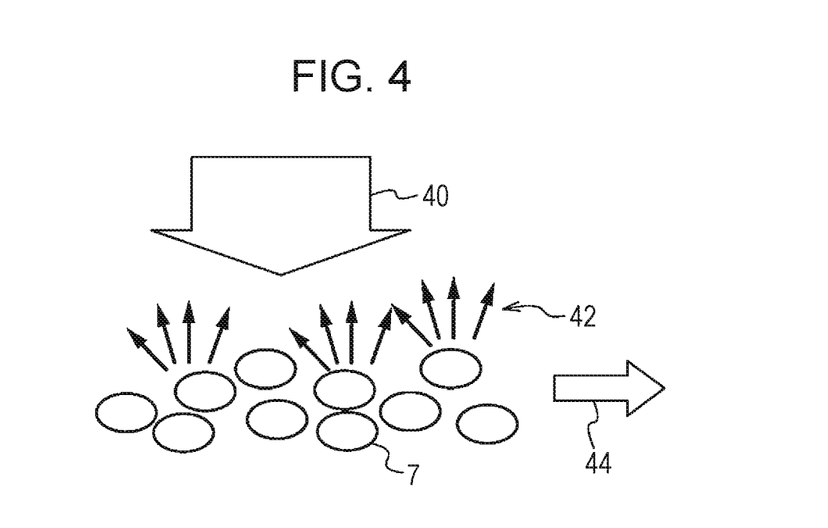
FIG. 4 is a schematic diagram used to explain speckles that occur when a blood vessel is irradiated with a laser beam.

FIG. 4 illustrates a case where the light-emitting element 1 emits the coherent light beam 40, such as a laser beam, toward blood cells 7, such as red blood cells, that move in the direction of an arrow 44. In this case, the laser beam is scattered by the blood cells 7 in various directions. The scattered light, which have different phases, interfere with each other randomly. Thus, a light intensity distribution having a random spotted pattern occurs. A light intensity distribution pattern formed in this way is referred to as a "speckle pattern".

As described above, because the blood cells 7 move in the blood vessel, the way in which light is scattered by the blood cells 7 changes, and the speckle pattern varies with time. Accordingly, the amount of light received by the light-receiving element 3 changes with time.

Figure 5:
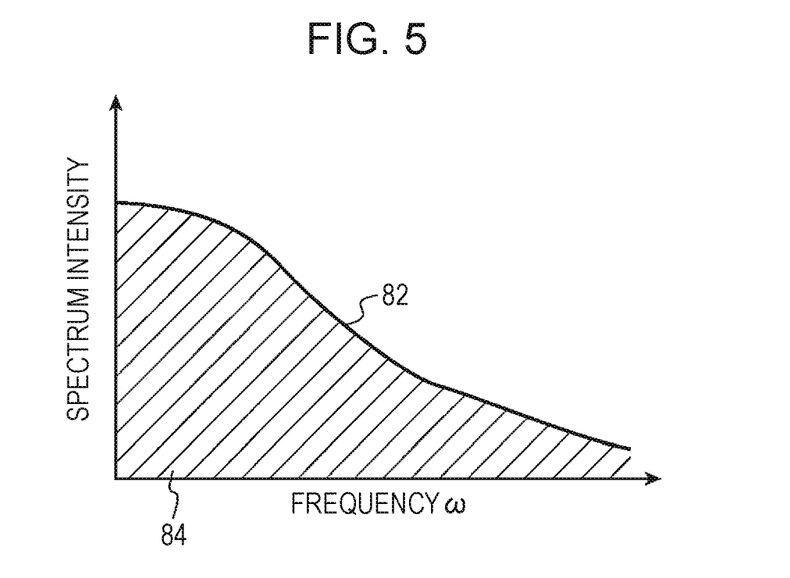
FIG. 5 is a graph illustrating one example of a spectrum distribution with respect to change in an amount of received light.

Next, an example of a method of obtaining blood flow information will be described. Referring to FIG. 2, when the time-series data of the amount of light received by the light-receiving element 3 is obtained, a part of the data in a predetermined unit time $T_0$ is cut out. By performing, for example, fast Fourier transform (FFT) on the data, a spectrum distribution for the frequency $\omega$ is obtained. FIG. 5 is a graph showing a curve 82 representing an example of the spectrum distribution for the frequency $\omega$ in the unit time $T_0$. In the graph of FIG. 5, the horizontal axis represents the frequency $\omega$, and the vertical axis represents the spectrum intensity.

The blood volume is proportional to a value obtained by normalizing, with respect to the total light amount, the area of power spectrum, which is represented by a hatched region 84 surrounded by the curve 82, the horizontal axis, and the vertical axis of the graph of FIG. 5. The blood velocity is proportional to the average frequency of the power spectrum represented by the curve 82. Therefore, the blood velocity is proportional to a value obtained by dividing the integral of the product of the frequency $\omega$ and the power spectrum at the frequency $\omega$ with respect to the frequency $\omega$ by the area of the hatched region 84.

The blood flow, which is the product of the blood volume and the blood velocity, is obtained by using the aforementioned formulas for calculating the blood volume and the blood velocity. The blood flow, the blood velocity, and the blood volume are examples of blood flow information. However, blood flow information is not limited to these.

Figure 6:
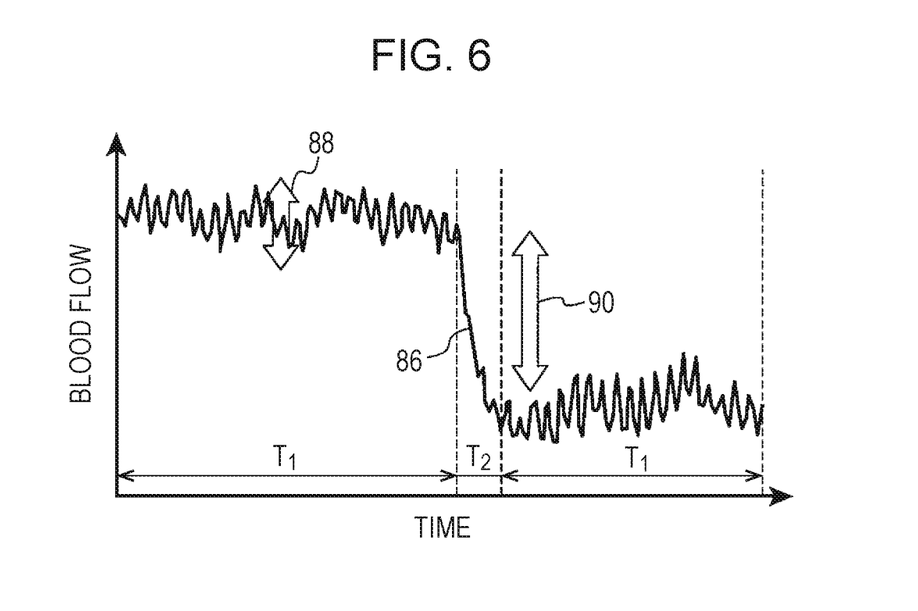
FIG. 6 is a graph illustrating one example of a change in the blood flow.

FIG. 6 is a graph showing a curve 86 representing an example of the calculated change in the blood flow per unit time $T_0$. In the graph of FIG. 6, the horizontal axis represents the time and the vertical axis represents the blood flow.

As illustrated in FIG. 6, the blood flow varies with time, and the trend of the variation is divided into two types. For example, a variation range 90 of the blood flow in an interval $T_2$ of FIG. 6 is larger than a variation range 88 of the blood flow in an interval $T_1$ of FIG. 6. Presumably this is because the change in the blood flow in the interval $T_1$ is mainly due to pulsation and the change in the blood flow in the interval $T_2$ is due to, for example, congestion.

As described above, it is known that the depth, beneath a skin, of a region that a blood flow sensor measures increases as the distance between the light-emitting element and the light-receiving element increases. In order to increase the amount of information necessary for diagnosis and health care, it is preferable to obtain living-body information at more than one depth.

Therefore, in the present exemplary embodiment, a light-receiving element is disposed at a position at different distances from plural light-emitting elements, and the light-emitting elements are controlled so that the light-emitting elements successively emit light beams. The blood flows at different depths in the living body are measured by using reflected light beams that are successively received by the light-receiving element.

Figure 7:
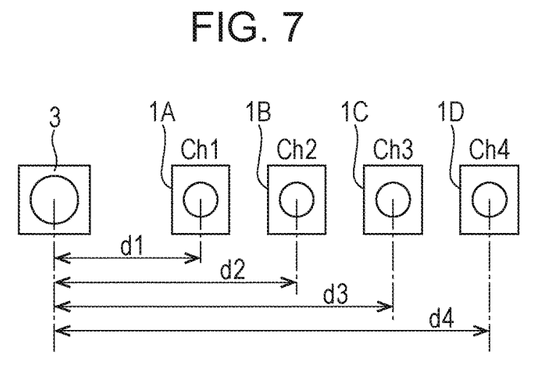
FIG. 7 is a plan view illustrating plural light-emitting elements and a light-receiving element according to a first exemplary embodiment.

FIG. 7 is a plan view illustrating an example of the arrangement of the plural light-emitting elements and the light-receiving element according to the present exemplary embodiment. FIG. 7 illustrates a case where four light-emitting elements 1A to 1D are used. The light-emitting elements 1A to 1D have the same characteristics. The number of light-emitting elements is not limited to four and may be appropriately determined in accordance with the number of depths at which living-body information is to be obtained. In the present exemplary embodiment, for example, surface-emitting lasers are used as the light-emitting elements 1A to 1D. Alternatively, edge-emitting lasers may be used. As described above, when measuring the blood flow, the spectrum distribution of light-receiving amount due to a beat signal is used. Therefore, preferably, laser devices that are capable of emitting light beams that easily generate beat signals are used as the light-emitting elements 1A to 1D.

As illustrated in FIG. 7, the light-emitting elements 1A to 1D and the light-receiving element 3 are arranged along a straight line. The distances d1 to d4 between the light-emitting elements 1A to 1D and the light-receiving element 3 differ from each other. To be specific, d1<d2<d3<d4. Although the light-emitting elements 1A to 1D and the light-receiving element 3 are arranged along a straight line in FIG. 7, it is not necessary that the light-emitting elements 1A to 1D be arranged along a straight line, provided that the distances d1 to d4 between the light-emitting elements 1A to 1D and the light-receiving element 3 differ from each other.

Figure 8:
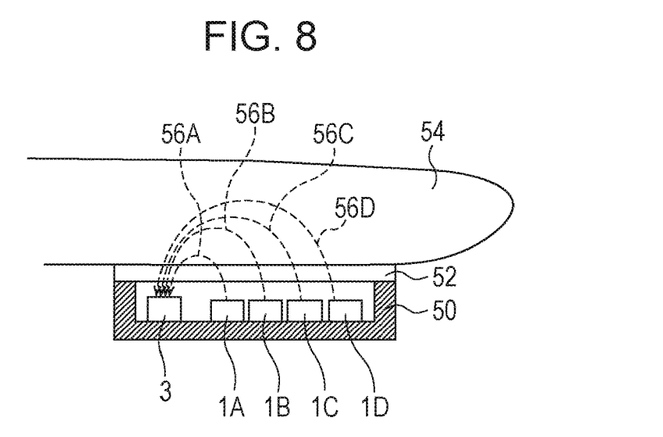
FIG. 8 illustrates a living-body information measuring device on which a fingertip is placed.

As illustrated in FIG. 8, the light-emitting elements 1A to 1D and the light-receiving element 3 are arranged in a row in a housing 50. A transparent plate 52 is disposed so as to face the light-emitting surfaces of the light-emitting elements 1A to 1D. A user places his/her fingertip 54 on the transparent plate 52 and performs measurement. As illustrated in FIG. 8, the light-emitting element 1A emits a light beam 56A, the light-emitting element 1B emits a light beam 56B, the light-emitting element 1C emits a light beam 56C, and the light-emitting element 1D emits a light beam 56D. When the paths of the light beams 56A to 56D in the fingertip 54 are compared, the depth that each of the light beams 56A to 56D reaches increases as the distance from the light-receiving element 3 to a corresponding one of the light-emitting elements 1A to 1D increases.

Figure 9:
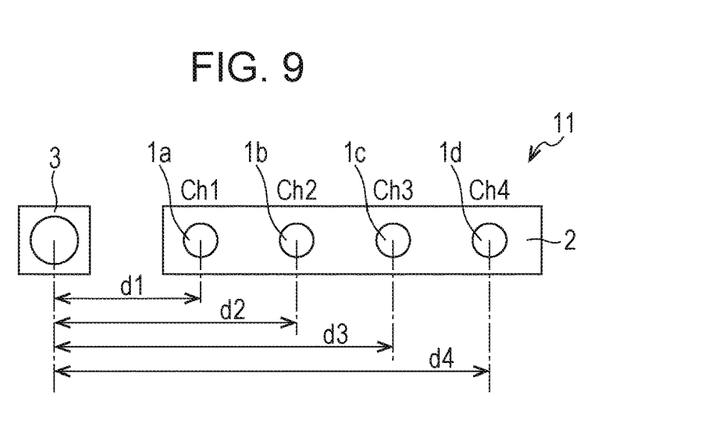
FIG. 9 is a plan view of a surface-emitting laser array.

As illustrated in FIG. 9, a surface-emitting laser array 11, in which plural light-emitting spots 1a to 1d are disposed on a single substrate 2, may be used.

Figure 10:
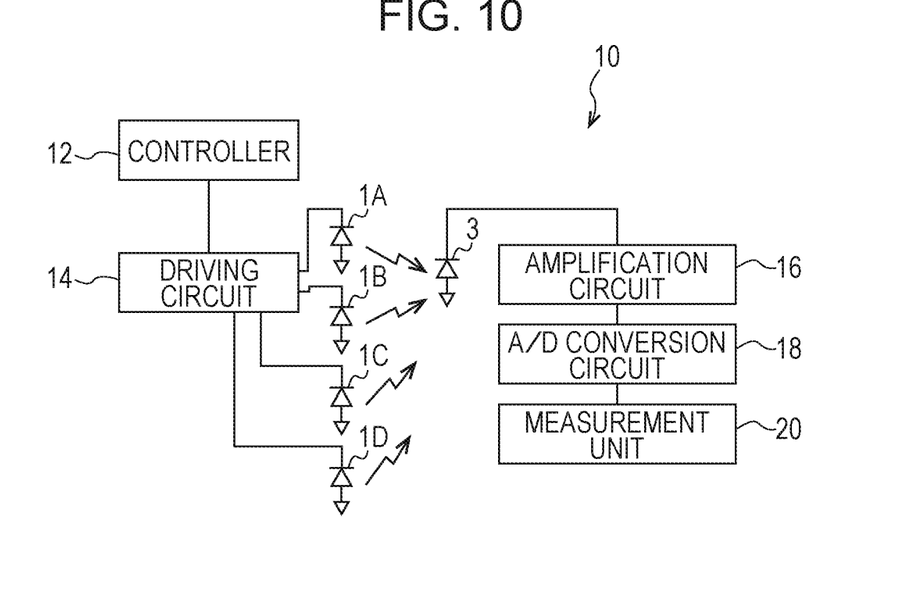
FIG. 10 is an exemplary block diagram of the living-body information measuring device.

FIG. 10 is an exemplary block diagram of a living-body information measuring device 10 according to the present exemplary embodiment.

As illustrated in FIG. 10, the living-body information measuring device 10 includes a controller 12, a driving circuit 14, an amplification circuit 16, an analog/digital (A/D) conversion circuit 18, a measurement unit 20, the light-emitting elements 1A to 1D, and the light-receiving element 3.

The driving circuit 14 includes a power supply circuit that supplies electric power to the light-emitting elements 1A to 1D. To the driving circuit 14, the controller 12 outputs a control signal for controlling the light-emission cycles and the light-emission periods of the light-emitting elements 1A to 1D.

When receiving the control signal from the controller 12, the driving circuit 14 supplies electric power to the light-emitting elements 1A to 1D to drive the light-emitting elements 1A to 1D in accordance with the light-emission cycles and the light-emission periods indicated by the control signal.

Figure 11:
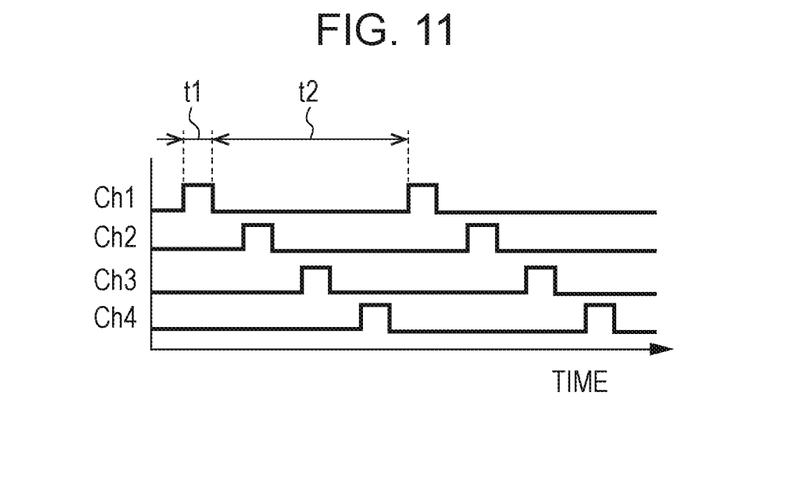
FIG. 11 is a timing chart of light-emission timings.

For example, as illustrated in FIG. 11, the driving circuit 14 repeatedly causes the light-emitting elements 1A (Ch1), 1B (Ch2), 1C (Ch3), and 1D (Ch4) to successively emit light beams each for a period t1 and to stop emitting a light beam for a period t2 while shifting the time at which the light-emitting elements 1A to 1D emit light beams.

The amplification circuit 16 amplifies a voltage, which corresponds to the intensity of light received by the light-receiving element, to a level within a specified input voltage range of the A/D conversion circuit 18. Here, for example, the light-receiving element 3 outputs a voltage corresponding to the intensity of received light. Alternatively, the light-receiving element 3 may output an electric current corresponding to the intensity of received light. In this case, the amplification circuit 16 amplifies the electric current, output from the light-receiving element 3, to a level within a specified input current range of the A/D conversion circuit 18.

The voltage amplified by the amplification circuit 16 is input to the A/D conversion circuit 18. The A/D conversion circuit 18 digitizes the amount of light received by the light-receiving element 3, which is represented by the voltage, and outputs the digitized amount of received light.

Figure 12:
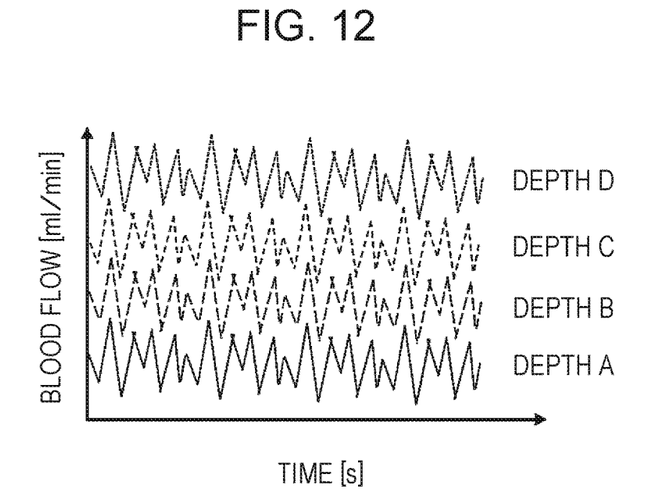
FIG. 12 is a graph representing blood flows at plural depths.

The amount of received light, which has been digitized by the A/D conversion circuit 18, is input to the measurement unit 20. The measurement unit 20 performs FFT on each of the amounts of light emitted from the light-emitting elements 1A to 1D and received by the light-receiving element 3 to calculate the spectrum distribution for the frequency ω. Then, the measurement unit 20 measures the blood flow of the living body by integrating the spectrum distribution with respect to the entire frequency ω. When the light-emitting elements 1A to 1D successively emit light beams at timings shown in FIG. 11, the amounts of the light beams emitted from the light-emitting elements 1A to 1D and received by the light-receiving element 3 are successively input to the measurement unit 20. The measurement unit 20 measures the blood flow by performing the aforementioned operation every time the amounts of received light are input. Thus, blood flows at plural depths are obtained as illustrated in FIG. 12.

As describe above, according to the present exemplary embodiment, the light-receiving element 3 is disposed at a position at different distances from the light-emitting elements 1A to 1D, and blood flows at plural depths of a living body are measured by using reflected light beams from the living body that are successively received by the light-receiving element 3. Therefore, blood flows at plural depths of the living body are obtained and living-body information useful for diagnosis and health care is obtained, in contrast to a case where a blood flow is obtained by emitting a light beam from a single light-emitting element and receiving a reflected light beam from the living body.

Second Exemplary Embodiment

Next, a second exemplary embodiment of the present invention will be described.

Figure 13:
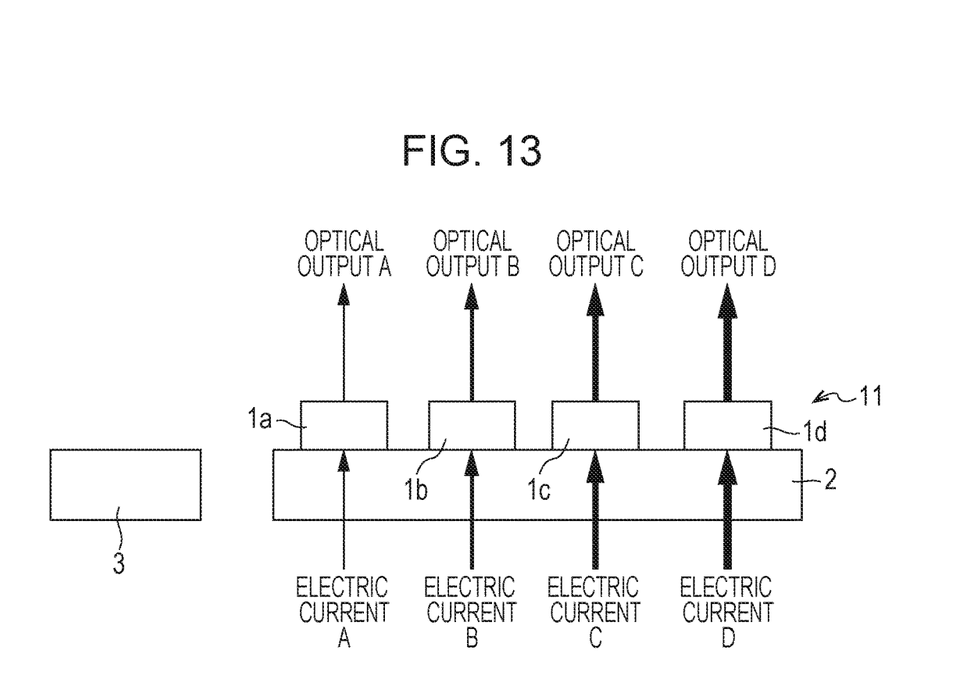
FIG. 13 is a side view of a surface-emitting laser array according to a second exemplary embodiment.

FIG. 13 is a side view of the surface-emitting laser array 11 according to the present exemplary embodiment. As described above, the surface-emitting laser array 11 includes plural luminous points 1a to 1d on the single substrate 2. Descriptions of the other components of the second exemplary embodiment, which are the same as those of the first exemplary embodiment, will be omitted.

In the present exemplary embodiment, the luminous points 1a to 1d are controlled so that a driving current for driving each luminous point decreases as the distance from the light-receiving element 3 to the luminous point decreases and the electric current for driving each luminous point increases as the distance from the light-receiving element 3 to the luminous point increases.

As illustrated in FIG. 13, the driving circuit 14 supplies electric currents A to D, for driving the luminous points 1a to 1d, to the luminous points 1a to 1d. The electric current A supplied to the luminous point 1a, which is at the shortest distance from the light-receiving element 3, is the smallest. The electric current D supplied to the luminous point 1d, which is at the longest distance from the light-receiving element 3, is the largest.

Thus, among optical outputs A to D from the luminous points 1a to 1d, the optical output A from the luminous point 1a, which is at the shortest distance from the light-receiving element 3, is the smallest; and the optical output D from the luminous point 1d, which is at the longest distance from the light-receiving element 3, is the largest. As the distance from the light-receiving element 3 to the luminous point increases, the distance that light propagates in the living body increases and the attenuation of the light increases. Therefore, by increasing the electric current supplied to each luminous point with increasing distance from the light-receiving element 3, variation in the amount of light emitted from the luminous points 1a to 1d and received by the light-receiving element 3 is suppressed.

Preferably, the values of the electric currents supplied to the luminous points 1a to 1d are set so that the amount of light emitted from each of the luminous points 1a to 1d and received by the light-receiving element 3 is within the dynamic range of the light-receiving element 3. In this case, living-body information at plural depths is obtained with high precision.

The magnitudes of the electric currents A to D may be changed in accordance with the type of living-body information to be measured. In this case, optical outputs suitable for the type of the measured living-body information are realized.

Third Exemplary Embodiment

Next, a third exemplary embodiment of the present invention will be described.

Figure 14:
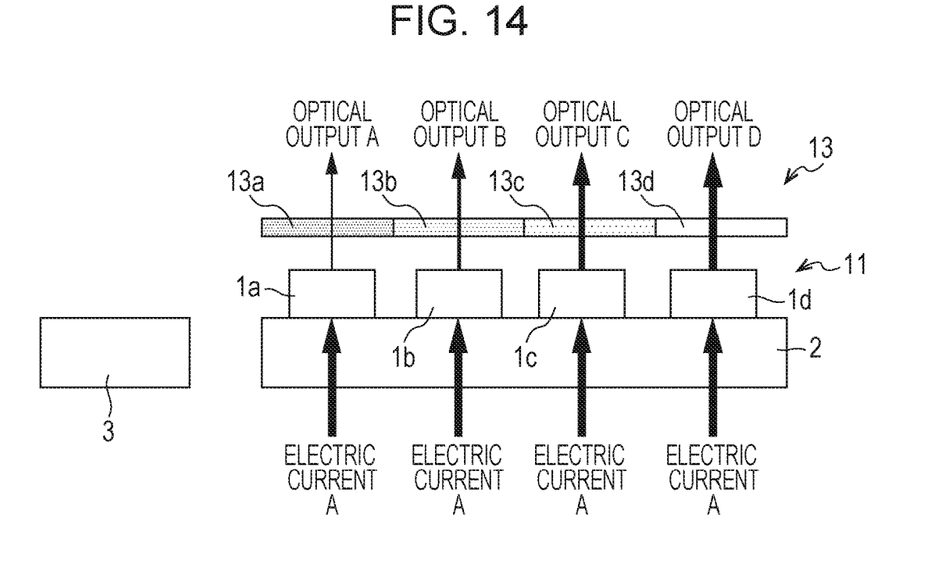
FIG. 14 is a side view of a surface-emitting laser array according to a third exemplary embodiment.

In the present exemplary embodiment, as illustrated in FIG. 14, an attenuating filter 13 is disposed on the optical output side of the surface-emitting laser array 11. Descriptions of the other components of the third exemplary embodiment, which are the same as those of the second exemplary embodiment, will be omitted.

The attenuating filter 13 attenuates light beams emitted from the luminous points 1a to 1d so that the attenuation ratio of a light beam emitted from each luminous point increases as the distance from the light-receiving element 3 to the luminous point decreases and the attenuation ratio of the light beam emitted from each luminous point decreases as the distance from the luminous point 3 to the luminous point increases. To be specific, the attenuating filter 13 includes a region 13a, through which a light beam emitted from the luminous point 1a passes; a region 13b, through which a light beam emitted from the luminous point 1b passes; a region 13c, through which a light beam emitted from the luminous point 1c passes; and a region 13d, through which a light beam emitted from the luminous point 1d passes. The attenuation ratios in the regions 13a, 13b, 13c, and 13d decrease in this order.

The driving circuit 14 supplies the same electric current A to the luminous points 1a to 1d. Thus, among the optical outputs A to D from the luminous points 1a to 1d, the optical output A from the luminous point 1a, which is at the shortest distance from the light-receiving element 3, is the smallest; and the optical output D from the luminous point 1d, which is at the longest distance from the light-receiving element 3, is the largest. As the distance from the light-receiving element 3 to the luminous point increases, the distance that light propagates in the living body increases and the attenuation of the light increases. Therefore, by disposing the attenuating filter 13, in which the attenuation ratio of light decreases with increasing distance from the light-receiving element 3, on the optical output side of the surface-emitting laser array 11, variation in the amount of light emitted from the luminous points 1a to 1d and received by the light-receiving element 3 is suppressed.

Preferably, the attenuation ratios of the regions of the attenuating filter 13 are set so that the amount of light emitted from each of the luminous points 1a to 1d and received by the light-receiving element 3 is within the dynamic range of the light-receiving element 3. In this case, living-body information at plural depths is obtained with high precision.

Fourth Exemplary Embodiment

Next, a fourth exemplary embodiment of the present invention will be described.

Figure 15:
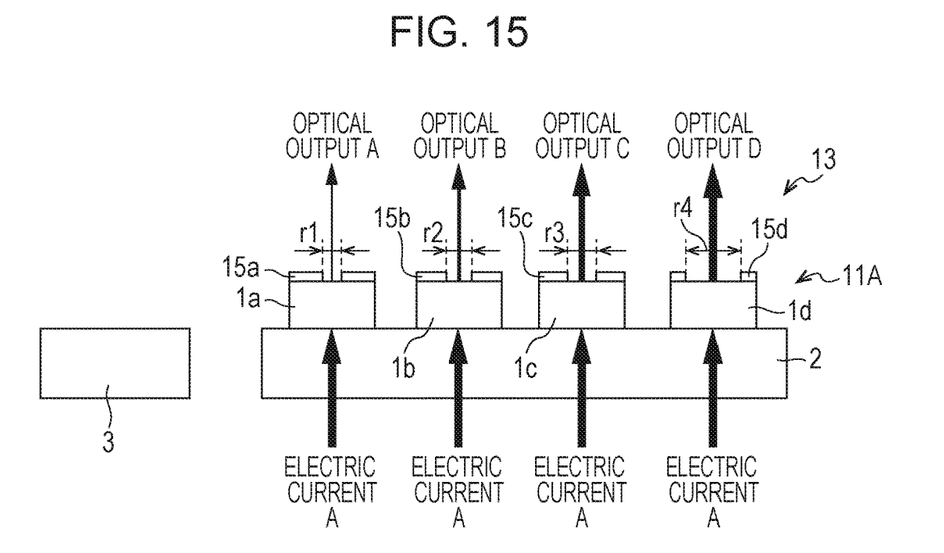
FIG. 15 is a side view of a surface-emitting laser array according to a fourth exemplary embodiment.

FIG. 15 illustrates a surface-emitting laser array 11A according to the present exemplary embodiment. Descriptions of the other components of the fourth exemplary embodiment, which are the same as those of the second exemplary embodiment, will be omitted.

As illustrated in FIG. 15, the luminous points 1a to 1d respectively include upper electrodes 15a to 15d. In the surface-emitting laser array 11A, the area of an opening in the upper electrode of each luminous point decreases as the distance from the light-receiving element 3 to the luminous point decreases, and the area of the opening in the upper electrode of each luminous point increases as the distance from the light-receiving element 3 to the luminous point increases. In the present exemplary embodiment, the luminous points 1a to 1d each have a circular shape in plan view as illustrated in FIG. 9. Likewise, the upper electrodes 15a to 15d and the openings of the upper electrodes 15a to 15d each have a circular shape in plan view. Accordingly, the diameter of the opening in the upper electrode of each luminous point of the light-receiving element 3 decreases as the distance from the light-receiving element 3 to the luminous point decreases, and the diameter of the opening in the upper electrode of the luminous point of the light-receiving element 3 increases as the distance from the light-receiving element 3 to the luminous point increases That is, as illustrated in FIG. 15, the diameter r1 of the opening in the upper electrode 15a of the luminous point 1a, which is at the shortest distance from the light-receiving element 3, is the smallest; and the diameter r4 of the opening in the upper electrode 15d of the luminous point 1d, which is at the longest distance from the light-receiving element 3, is the largest.

The driving circuit 14 supplies the same electric current A to the luminous points 1a to 1d. Thus, among the optical outputs A to D from the luminous points 1a to 1d, the optical output A from the luminous point 1a, which is at the shortest distance from the light-receiving element 3, is the smallest, and the optical output D from the luminous point 1d, which is at the longest distance from the light-receiving element 3, is the largest. As the distance from the light-receiving element 3 to each luminous point increases, the distance that light propagates in the living body increases and the attenuation of the light increases. Therefore, by increasing the diameter of the opening in the upper electrode with increasing distance from the light-receiving element 3, variation in the amount of light emitted from the luminous points 1a to 1d and received by the light-receiving element 3 is suppressed.

Preferably, the areas of the openings (the diameters of the openings) in the upper electrodes are set so that the amount of light emitted from each of the luminous points 1a to 1d and received by the light-receiving element 3 is within the dynamic range of the light-receiving element 3. In this case, living-body information at plural depths is obtained with high precision.

Fifth Exemplary Embodiment

Next, a fifth exemplary embodiment of the present invention will be described.

Figure 16:
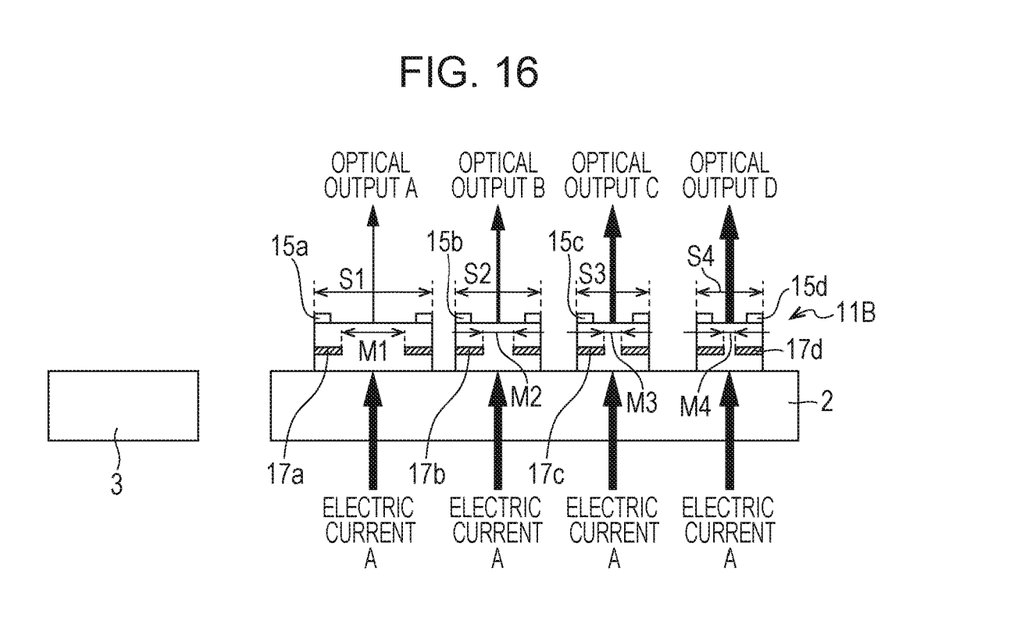
FIG. 16 is a side view of a surface-emitting laser array according to a fifth exemplary embodiment.

FIG. 16 illustrates a surface-emitting laser array 11B according to the present exemplary embodiment. Descriptions of the other components of the fifth exemplary embodiment, which are the same as those of the second exemplary embodiment, will be omitted.

The luminous points 1a to 1d of the surface-emitting laser array 11B according to the present exemplary embodiment each have a circular shape in plan view. Oxidized regions 17a to 17d each have an annular shape that surrounds a non-oxidized region in plan view. The diameter of each luminous point increases as the distance from the light-receiving element 3 to the luminous point decreases, and the diameter of each luminous point decreases as the distance from the light-receiving element 3 to the luminous point increases. That is, as illustrated in FIG. 16, the diameter S1 of the luminous point 1a, which is at the shortest distance from the light-receiving element 3, is the largest; and the diameter S4 of the luminous point 1d, which is at the longest distance from the light-receiving element 3, is the smallest.

Oxidization times required to form the oxidized regions 17a to 17d of the luminous points 1a to 1d are the same for all the luminous points 1a to 1d. Therefore, oxidation distances of the oxidized regions 17a to 17d are substantially the same. Accordingly, as the diameters of the luminous points 1a to 1d differ from each other, the diameters of the non-oxidized regions surrounded by the oxidized regions 17a to 17d, that is, the mesa sizes differ from each other.

That is, as illustrated in FIG. 16, the mesa size M1 of the luminous point 1a, which is at the shortest distance from the light-receiving element 3, is the largest; and the mesa size M4 of the luminous point 1d, which is at the longest distance from the light-receiving element 3, is the smallest.

The driving circuit 14 supplies the same electric current A to the luminous points 1a to 1d. Thus, among the optical outputs A to D from the luminous points 1a to 1d, the optical output A from the luminous point 1a, which is at the shortest distance from the light-receiving element 3, is the smallest, and the optical output D from the luminous point 1d, which is at the longest distance from the light-receiving element 3, is the largest. As the distance from the light-receiving element 3 to the luminous point increases, the distance that light propagates in the living body increases and the attenuation of the light increases. Therefore, by increasing the mesa size with increasing distance from the light-receiving element 3, variation in the amount of light emitted from the luminous points 1a to 1d and received by the light-receiving element 3 is suppressed.

Figure 17:
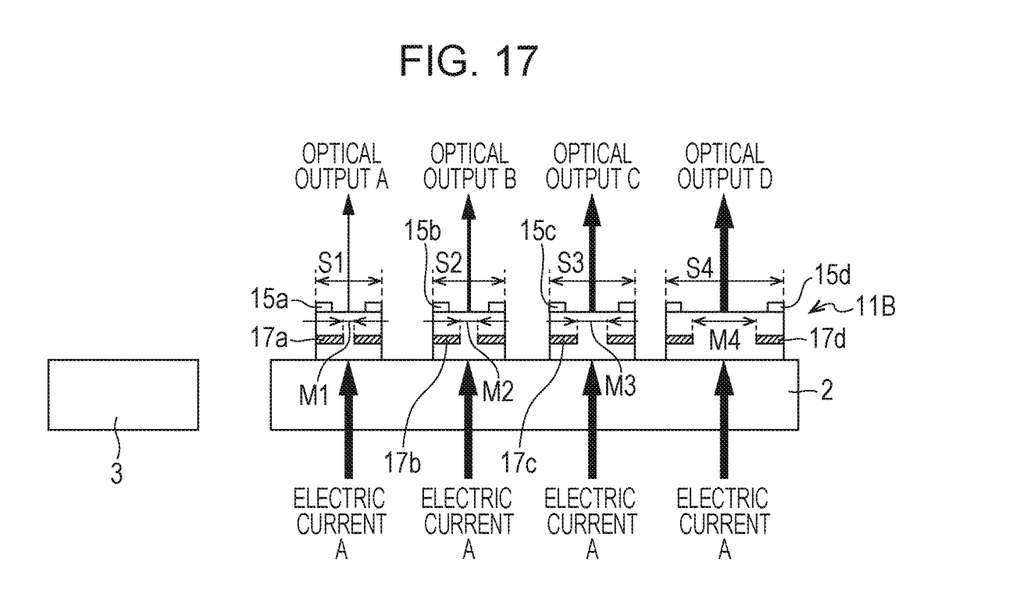
FIG. 17 is a side view of a surface-emitting laser array according to a modification of the fifth exemplary embodiment.

Typically, the light-emitting amount decreases as the mesa size increases. However, when the driving electric current is increased, the light-emitting amount may increase as the mesa size increases. Therefore, as illustrated in FIG. 17, depending on the driving conditions, the relationship among the mesa sizes of the luminous points may become opposite to the aforementioned relationship. Preferably, the mesa sizes (the diameters of the non-oxidized regions) of the luminous points are set so that the amount of light emitted from each of the luminous points 1a to 1d and received by the light-receiving element 3 is within the dynamic range of the light-receiving element 3. In this case, living-body information at plural depths is obtained with high precision.

In each of the exemplary embodiments described above, the living-body information measuring device 10 is used to measure the blood flow as living-body information. However, as described above, the living-body information measuring device 10 may be used to measure the blood velocity, instead of the blood flow. The pulse rate is measured by using the amount of light received by the light-receiving element 3, because the amount of light received by the light-receiving element 3 changes due to pulsation of an artery. The photoplethysmogram is measured by calculating the second derivative of a waveform obtained by measuring the change in the pulse rate in chronological order. The photoplethysmogram is used, for example, to estimate a vascular age or to diagnose arteriosclerosis. The living-body information measuring device 10 may be used to measure a blood component (blood sugar level or the like), the blood pressure, and the like.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A living-body information measuring device comprising:
    a plurality of light-emitting elements;
    a light-receiving element that is disposed at a position at different distances from the light-emitting elements, wherein the light-receiving element is configured to receive reflected light beams that are reflected from a living body in response to the light-emitting elements emitting light beams toward the living body;
    a control unit configured to control the light-emitting elements so that the light-emitting elements successively emit the light beams; and
    a measurement unit configured to measure living-body information at a plurality of depths in the living body by using the reflected light beams that are successively received by the light-receiving element,
    wherein a mesa size of each light-emitting element decreases as the distance from the light-receiving element to the light-emitting element decreases and the mesa site of each light-emitting element increases as the distance from the light-receiving element to the light-emitting element increases.

2. The living-body information measuring device according to claim 1,
    wherein the control unit is configured to control the plurality of light-emitting elements so that an electric current for driving each light-emitting element decreases as the distance from the light-receiving element to the light-emitting element decreases and the electric current for driving each light-emitting element increases as the distance from the light-receiving element to the light-emitting element increases.

3. The living-body information measuring device according to claim 1, further comprising:
    an attenuating filter configured to attenuate the light beams emitted from the plurality of light-emitting elements so that an attenuation ratio of the light beam emitted from each light-emitting element increases as the distance from the light-receiving element to the light-emitting element decreases and the attenuation ratio of the light beam emitted from each light-emitting element decreases as the distance from the light-receiving element to the light-emitting element increases.

4. The living-body information measuring device according to claim 1,
    wherein an area of an opening in an upper electrode of each light-emitting element decreases as the distance from the light-receiving element to the light-emitting element decreases and the area of the opening in the upper electrode of each light-emitting element increases as the distance from the light-receiving element to the light-emitting element increases.

5. The living-body information measuring device according to claim 1,
wherein the plurality of light-emitting elements are a plurality of surface-emitting lasers or are a plurality of light-emitting spots disposed on a single substrate of a surface-emitting laser array.

6. The living-body information measuring device according to claim 1,
wherein the living-body information includes at least one of a blood flow, a blood velocity, a blood volume, a pulse rate, a photoplethysmogram, a blood component, and a blood pressure of the living body.

* * * * *